US006681772B2

(12) United States Patent
Atwater et al.

(10) Patent No.: US 6,681,772 B2
(45) Date of Patent: Jan. 27, 2004

(54) HAND, WRIST AND FOREARM DEVICE PATIENTS DURING SURGERY

(76) Inventors: Kim A. Atwater, 1201-44th Pl. SE., Washington, DC (US) 20019; Marian J. Bryant, 404 Wompatuck Ct., Silver Spring, MD (US) 20905

( * ) Notice: Subject to any disclaimer, the term of this patent is extended or adjusted under 35 U.S.C. 154(b) by 0 days.

(21) Appl. No.: 10/252,204

(22) Filed: Sep. 23, 2002

(65) Prior Publication Data

US 2003/0056793 A1 Mar. 27, 2003

Related U.S. Application Data

(60) Provisional application No. 60/324,092, filed on Sep. 24, 2001.

(51) Int. Cl.[7] .................................................. A61F 5/37
(52) U.S. Cl. ......................... 128/878; 128/879; 602/20; 602/21
(58) Field of Search ................................ 128/846, 877, 128/878, 879, 882, 888; 602/5, 20, 21, 22

(56) References Cited

U.S. PATENT DOCUMENTS

| 685,574 | A | * | 10/1901 | Comboie | |
| 3,415,244 | A | * | 12/1968 | Block | |
| 3,701,349 | A | * | 10/1972 | Larson | 602/13 |
| 3,955,565 | A | * | 5/1976 | Johnson | 602/13 |
| 5,279,574 | A | * | 1/1994 | Forren | 128/879 |
| 5,441,058 | A | * | 8/1995 | Fareed | 602/20 |
| 5,682,905 | A | * | 11/1997 | Grant | 128/878 |

* cited by examiner

*Primary Examiner*—Michael A. Brown
(74) *Attorney, Agent, or Firm*—Bradford E. Kile; Kile Goekjian Reed & McManus PLLC

(57) ABSTRACT

A hand, wrist and forearm device for patients during surgery, including a pair of mating shells which fit about the patient's hand, and wrist and forearm. Each shell has a generally accurate lateral section wrist and forearm channel and a larger, generally accurate longitudinal section hand enclosure. The two shells are loosely hinged together along one edge, with a mutually mating closure provided along the edge generally opposite the hinges. The interior is preferably lined with removable padding, such as gel packs, viscoelastic material in order to apply light pressure to the hand and stabilize the position of surgical device on the hand. The pressure of the removable padding also provides a light outward pressure to stabilize the two halves of the assembly during use.

15 Claims, 4 Drawing Sheets

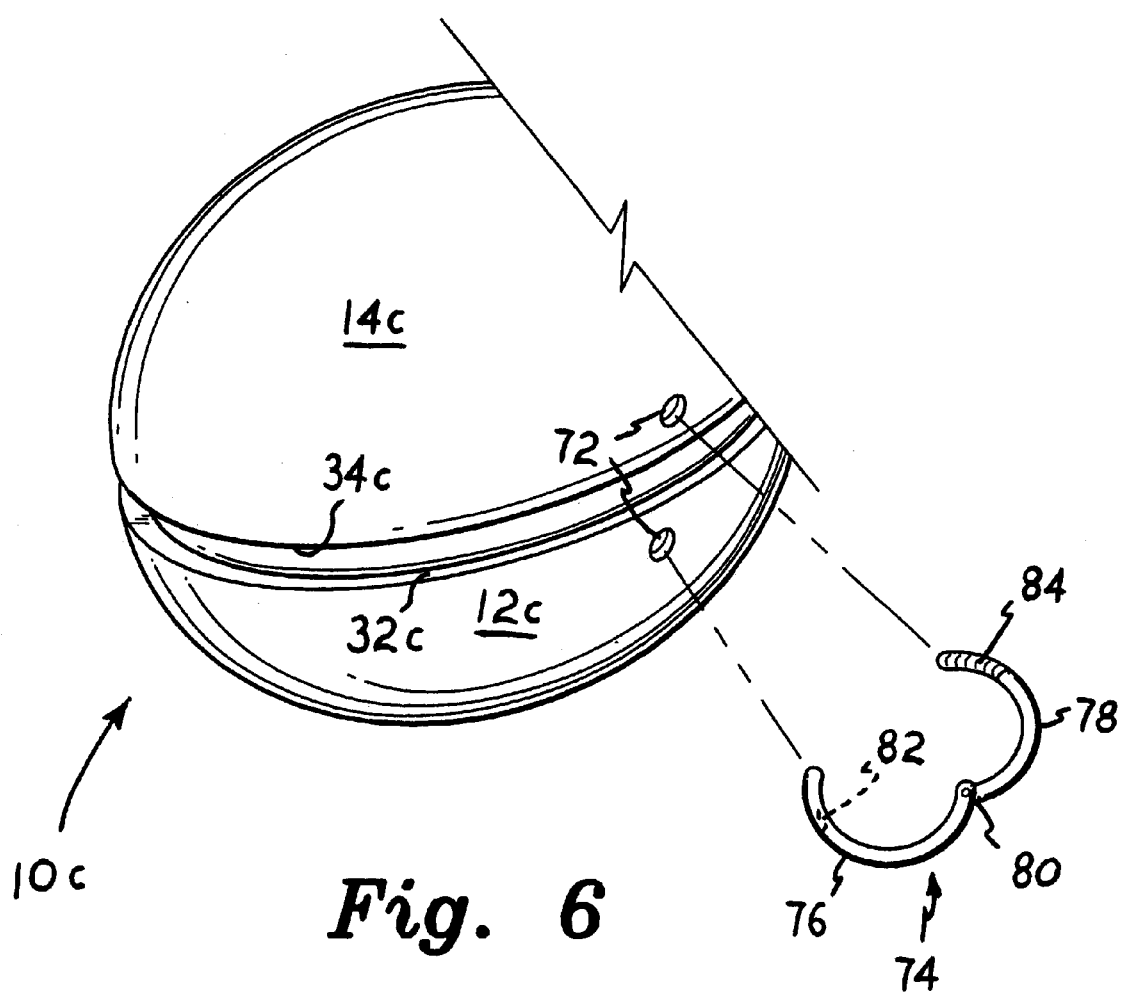

HAND, WRIST AND FOREARM DEVICE PATIENTS DURING SURGERY

PROVISIONAL APPLICATION AND RELATED PATENTS

This application claims the benefit of U.S. Provisional Application No. 60/324,092, by applicant's herein, as previously filed Sep. 24, 2001 and pertains to the field of medicine and surgery, and more specifically to devices for the hand, wrist and forearm of an unconscious anesthetized patient during surgery. Other devices in the general category of the subject invention are disclosed, for example, in U.S. Pat. No. 5,785,057 entitled "Medical Positioning Device" and U.S. Pat. No. 6,101,650 entitled "Recessed Arm Board."

BACKGROUND OF THE INVENTION

DESCRIPTION OF THE FIELD OF THE INVENTION AND RELATED ART

Surgical procedures have evolved into a broad range of different types of operations, with patient positioning depending upon the specific procedure to be accomplished. While most general surgery is performed on a supine patient under the influence of a general anesthetic, other types of surgery require the patient to be positioned in other than a supine position, with hands and arms extended beside or tucked along the side of the patient. An example is the lithotomy position, wherein a patient is generally positioned in a modified supine position with the hips and knees flexed and the legs supported by canvas straps or stirrups, the arms and hands being placed beside the patient, often on arm boards, or loosely cradled over the lower abdomen and secured by the lower end of a blanket. Occasionally the patient may incur injury to the hands through improper positioning of the arms and hands, through pressure when a surgeon leans over and inadvertently bears against the hand, or through crush injuries when the leg portion of the surgical table is raised after the surgery is completed. During surgery a patient is unusually very vulnerable, as the patient is under anesthesia and normal pain warning reactions are blocked.

The bones and other structure of the hands are some of the more fragile components of the human body, and oftentimes inadvertent pressure upon one or both hands, can lead to damage to the hands in the form of a broken bone or pulled tendon, soft tissue, or nerve damage, in addition to transient ischemic problems due to loss of circulation. Such problems are, of course, extremely difficult for a patient, who is often bedridden after surgery and who may have no significant ability to perform any physical act other than with his or her hands and arms. Injury to a patient's hands may deprive the patient of the only other physical activity available until the primary surgical healing process is well underway. Of course, such extra incapacity is a distraction to a positive emotional attitude of the patient during recovery. The cost of inadvertent hand and arm injuries to patients during surgery can be considerable, as the medical profession has a duty of great care during such operations, when the unconscious patient is totally at the mercy of the medical staff performing the procedure.

Accordingly, a need exists for a device which may be applied to the hand(s), wrist(s) and lower arm(s) of a patient who is to experience general anesthesia in order to isolate the extremities of the patient from compression or other damage due to inadvertent pressure upon the hands, wrists and lower arm as the patient is positioned prior to, during, and/or after a surgical procedure.

In the past certain devices have been known to locate or position a patient's arm and hand during surgery. In this, U.S. Pat. No. 5,785,057 to Fischer, titled "Medical Positioning Device," describes various embodiments of a device for immobilizing an arm of a surgical patient. The various embodiments each include a downwardly extending flange, with a lateral flange extending inwardly there from. The lateral flange is placed beneath the mattress of a surgical table, to hold the device (and the patient's arm) immobile during surgery. This positioning device is fixed relative to the surgical table. Accordingly, a patient using this device can not be easily moved or turned as required during many preoperative, operative, and/or postoperative periods, without removing the hand(s) from the channel(s) or disassembling the apparatus.

U.S. Pat. No. 6,101,650 issued Omdal et al., titled "Recessed Arm Board," describes a generally trough shaped device having a squared, U-shaped cross section with a flange extending laterally from the upper edge of one side. The flange is placed beneath the patient or a pad on the operating table with the patient's arm being allowed to rest within the trough. No padding or upper closure is disclosed and in fact, the fingers extend beyond the distal end of the device. The Omdal et al. device like the Fischer '057 positioning unit does not permit movement of a patent during surgery.

The foregoing noted limitations regarding previously known surgical hand, wrist and forearm positioning and isolating devices, while significant, demonstrate that room for worthwhile improvement remains.

OBJECTS OF THE INVENTION

Accordingly, it is a principal object of the invention to provide a hand, wrist and forearm device for patients during surgery, operable to isolate a patient's hand, wrist and lower arm from inadvertent damage or injury during a surgical procedure.

It is a further object of the invention to form the hand protector with each shell having a generally elliptical lateral section wrist securing portion, widening to a generally semi-accurate longitudinal section hand enclosure portion, with the two shells being loosely hinged together.

Still another object of the invention is to provide a series of loosely fitting hinges along one side of the two shells, with a series of mutually engaging fasteners along the opposite side for securing the two shells about the wrist and hand of the patient.

An additional object of the invention is to provide a softly padded liner or cushioning within each shell half, to apply alight pressure to the hand enclosed therein and further to urge the two shell halves outwardly to stabilize the assembly.

Yet another object of the invention is to form the liner or cushioning of a gel pack material, with the liner or cushioning being removably installed within each shell or half.

It is an object of the invention to provide improved elements and arrangements thereof in an apparatus for the purposes described which is inexpensive, dependable and fully effective in accomplishing its intended purposes.

While the invention is specifically designed for patients who undergo surgical procedures under general anesthesia, it should be noted that the subject invention may also find worthwhile application in an intensive care, geriatric, and/or pediatric environment where isolation and control of a patient's hand, wrist, or forearm is desired.

SUMMARY OF THE INVENTION

The present invention is a hand, wrist and lower arm device, particularly suitable for use by patients undergoing surgical procedures and subject to general anesthesia. Medical personnel do their best to ensure that no harm is done to the patient during the operation, by properly positioning arms and legs during the procedure so they are not twisted or otherwise injured during the procedure. However, oftentimes the hands, wrist and lower arms are subject to some pressure or damage as the surgeon and/or other medical staff leans over the patient during the surgical procedure. It may also be necessary to turn or reposition the patient before, during, and/or after the operation, e.g., to ensure proper drainage, etc., which may result in a limb being trapped beneath the body of the unconscious patient.

When this occurs, the anesthetized patient generally cannot move or turn normally, and in fact may be restrained to preclude damage to fresh sutures, inadvertent removal of an intravenous line, etc. Under such circumstances, circulation may be impaired for a critically long time in the trapped extremity, and/or damage may occur to the relatively small bones and relatively fragile tissues of the extremity if the hand is not properly positioned.

The present invention provides a solution to the above problem, in the form of a hand, wrist and lower arm device secures about the wrist of the patient to secure the patient's hand, wrist and lower arms. The patient's extremity is thus protected from crushing, twisting, and/or circulatory injury during surgery. Normally, a hand device would be applied to each hand of a patient resting in a supine position with the hands tucked beside the patient, depending upon the surgical procedure and position of the patient. However, the present hand protector invention may be applied singly to one hand, if the opposite hand is the subject of a surgical procedure.

The present hand device comprises a pair of rigid, mating shells which fit loosely together to enclose the hand, wrist and lower arm of a patient. Each shell has a generally accurate lateral section wrist securing portion, which widens to form a larger, generally semi-accurate longitudinal section hand enclosure portion. The two mating halves are generally mirror images of one another and may be formed from a common mold or form, thus simplifying manufacturing. The two halves are loosely hinged together along one edge thereof, with complementary fastener mean being provided along the mating edges opposite the hinges. The interior of each half is lined with a soft, resilient padding or cushioning material, such as gel packs, in order to preclude any contact injury to the enclosed hand against the interior of the rigid shell. The two halves secure loosely together, with the interior padding taking up the space between the interiors of the shells and an enclosed hand, waist and forearm. The padding or cushioning applies light pressure to the patient's extremity, gently holding the hand in a loosely spread position, while simultaneously applying slight outward pressure to the outer shells, in order to stabilize the shells in their assembled configuration.

BRIEF DESCRIPTION OF THE DRAWINGS

Other objects and advantages of the present invention will become apparent from the following detailed description of preferred embodiments thereof taken in conjunction with the accompanying drawings, wherein:

FIG. 6 is a broken away perspective view of yet another embodiment closure means for the surgical device, incorporating a split ring closure mechanism.

DETAILED DESCRIPTION OF THE PREFERRED EMBODIMENTS

The present invention comprises a hand, wrist and forearm device for encasing a patient's extremely during surgery, when the patient is under general anesthesia and is incapable of sensing any discomfort or pain resulting from an improperly positioned limb. In operation, one of the subject surgical devices is placed upon each hand, wrist and forearm of a patient for surgery, to isolate the hands, wrists and forearm against inadvertent pressures from the surgeon and/or medical staff as they operate, or during adjustment of the surgical table which may bring pressure to bear on the patient's extremities, etc.

Figure 1:
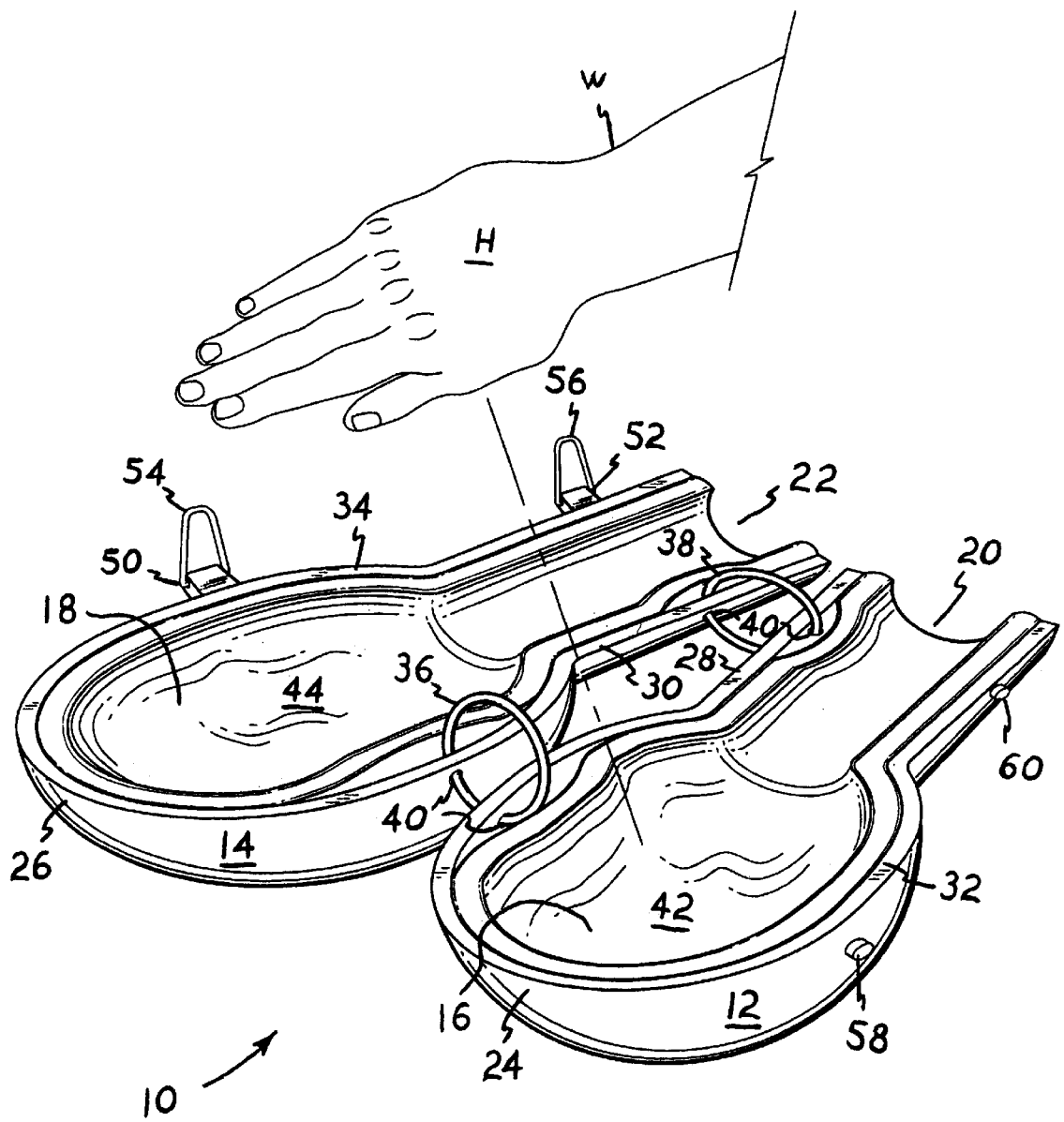
FIG. 1 is perspective view of a surgical hand, wrist and forearm device for patients during surgery according to a presently preferred embodiment of the invention, showing the direction of placement of a patient's hand, wrist and forearm within the device.
Figure 2:
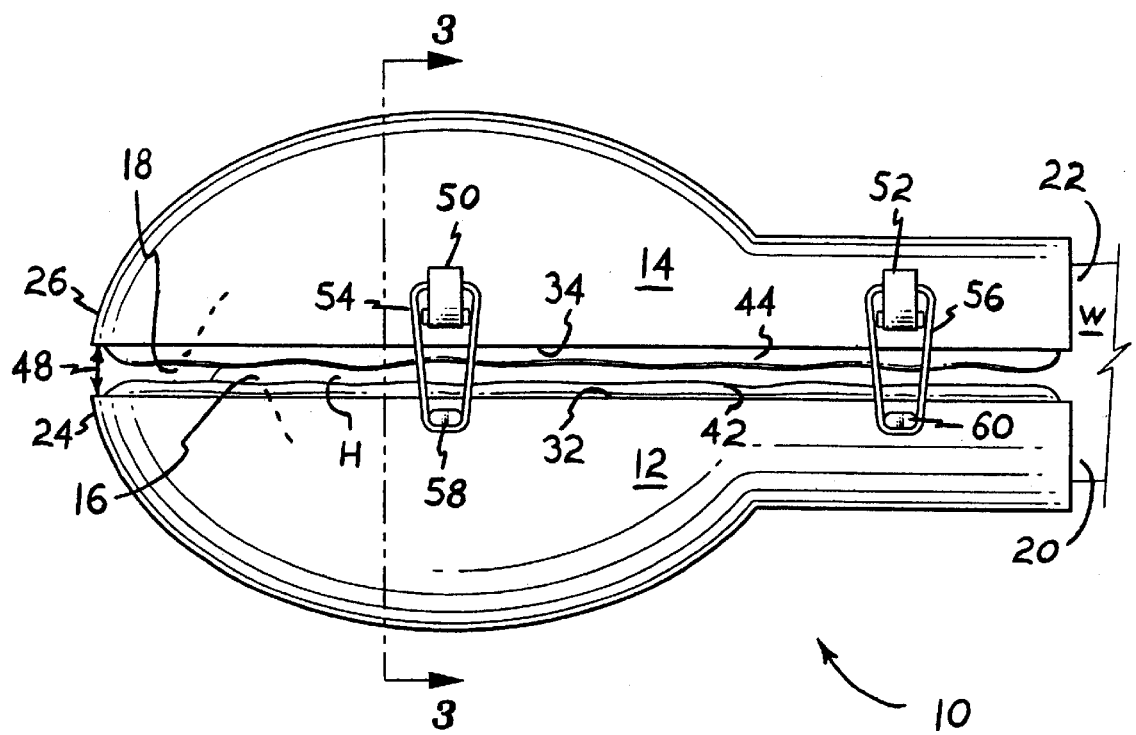
FIG. 2 is a side elevation view of the surgical device of FIG. 1, showing a closed and latched configuration thereof.
Figure 3:
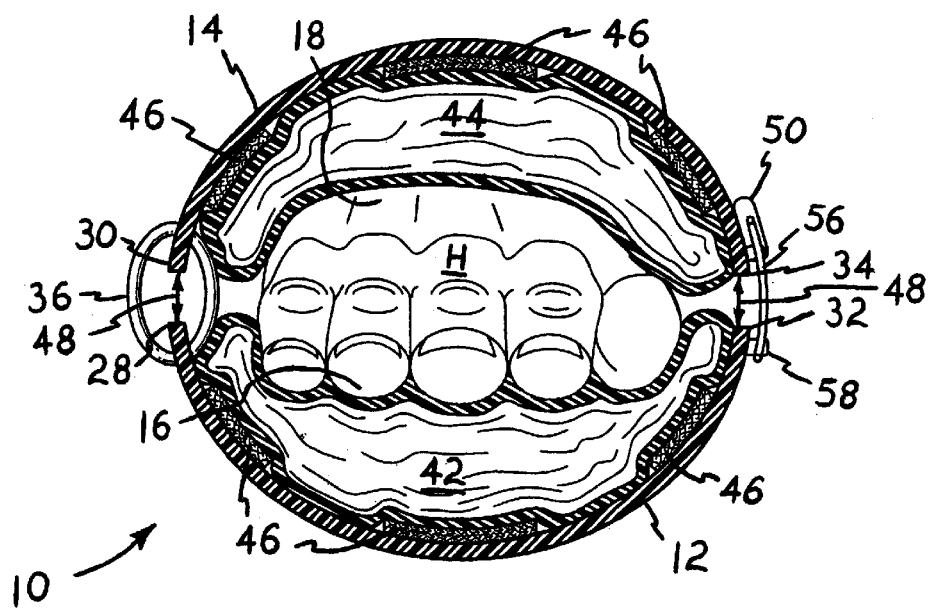
FIG. 3 is a cross sectional view taken along section line 3—3 of FIG. 2, illustrating placement of a surgical patient's hand within the subject device.

FIGS. 1 through 3 of the drawings provide illustrations of a first embodiment of the present surgical hand, wrist and forearm device, designated generally by the reference numeral 10. The surgical device 10 comprises opposite first and second shells, respectively 12 and 14, with each of the shells 12 and 14 being formed of a rigid material, such as a dense plastic. The specific material is not critical, except that: (1) it must be sufficiently rigid as to maintain its shape under pressure so as to insulate a hand, wrist and forearm placed therein from crushing or other injuries, and (2) the material preferably should be able to withstand sterilization procedures. High density plastics of various types have been found to meet the above requirements, depending upon their wall thicknesses. However, other materials such as corrosion resistant metals (stainless steel, aluminum, etc.) may be used if desired.

Each shell 12 and 14 forms a concave hand receptacle or enclosure, respectively 16 and 18, with a smaller concave wrist and forearm passage end, respectively 20 and 22, extending therefrom. The hand enclosure portions 16 and 18 preferably form a generally accurate or elliptical shape along their longitudinal sections, i.e., between their wrist passage ends 20, 22 and opposite distal closed finger ends 24, 26. The hand enclosure or receptacle portions 16 and 18 may also have a semi-elliptical or accurate cross sectional shape as well, as do the wrist and forearm passage portions 20 and 22. Preferably, the two shells 12 and 14 are laterally symmetrical, as shown from the lateral cross section of FIG. 3, and are identical to one another, so no consideration is required for top and bottom orientation. While the present shells 12 and 14 have been described as having generally semi-elliptical shapes, it will be understood that this description encompasses such related shapes as ovals, semi-circular, shapes, etc., so long as the shapes are configured to fit loosely about a surgical patient's hand.

Each of the two shells 12 and 14 has a lateral hinge connection edge or hinge line, respectively 28 and 30, and an opposite latch or closure edge, respectively 32 and 34.

The hinge attachment comprises at least one hinge, while there are preferably two hinges, with a first hinge connecting the hinge edges of the two hand receptacle portions 16 and 18 and a second hinge connecting the hinge edges of the two wrist and forearm passages 20 and 22 of the two shells 12 and 14.

As the hinge lines or edges 28 and 30 are not linear, but form a curve along the hand receptacle portions 16 and 18 of each shell 12 and 14, the two hinges preferably provide a relatively loose connection between the two shells 12 and 14 in order to avoid binding and interference along the two curved mating hinge edges 28 and 30. While a relatively complex hinge configuration could be adapted to provide a hinge attachment with no play, and still allow for the non-linear relationship between the two hinge lines 28 and 30 when the device is open, such a complex hinge arrangement would add to the cost of the device, would be more prone to failure, and would be more difficult to clean and sterilize.

The present invention solves this problem by means of a first and second hinge ring, respectively 36 and 38, which pass through holes or hinge passages 40 formed adjacent the two hinge edges 28 and 30 of the two shells 12 and 14. The two hinge rings 36 and 38 have inside diameters sufficient to allow the two shells 12 and 14 to have a significant amount of play relative to one another, thus allowing for relative freedom of movement of the non-linear and non-parallel hinge lines 28 and 30 of the shells 12 and 14 when they are open. This also allows some looseness or play along the hinge lines 28 and 30 when the two shells 12 and 14 are closed, but this is compensated for by the latch arrangement along the latch or closure edges 32 and 34, and more particularly by the fit of the patient's hand and wrist within the two shells 12 and 14 when they are closed, along with appropriate padding or cushioning material, described below, which is used to line each shell 12 and 14.

Each shell 12 and 14 includes a resilient cushioned liner, respectively 42 and 44, disposed therein. These liners 42 and 44 provide cushioning or padding between the relatively hard walls of the two shells 12 and 14 and the hand "H" placed therein, thereby precluding abrasions or other injuries to the hand "H" and wrist "W" when the present surgical device 10 is installed. The liners 42 and 44 also take up the remaining volume within the closed shells 12 and 14, in order to preclude excessive play or looseness of the hand "H" therein and to position and hold the hand "H" properly.

The two liners 42 and 44 are preferably removably installed within their respective shells 12 and 14, as by the conventional mating hook and loop fastening material 46 shown in section in FIG. 3 of the drawings. This allows the cushioning or padding material 42 and 44 to be removed in order to facilitate sterilization of all components of the present invention, and/or for replacement of the lining material 42 and 44 due to wear, or for installation of; thicker or thinner padding as required for a given surgical patient's hand. Preferably, the cushioning linings 42 and 44 are formed from gel packs, in order to conform closely to the contours of the patient's hand placed therein and thereby stabilize the position of the hand, as shown most clearly in the cross sectional view of FIG. 3. However, other padding or cushioning materials may be used as desired. In this, the material made be selected from a variety of visco-elastic compositions provided that there is a combination of conformability, resistance to extrusion, softness and compatibility with the surface of a patient's hand, wrist and forearm during surgery. One operative visco-elastic material is marketed in association with the trademark Tempur by the Tempur-Pedic company of Lexington, Ky. The lining material may be disposable or reusable provided that it can be sterilized. The liner may also be a foam composition enrobed within a sterile cloth or paper enclosure which may be removed from the cushion material and discarded so that the cushioning material, per se, may be reused following surgery.

The two liner cushions 42 and 44 are preferably relatively thick, in order to reduce the included volume of the two shells 12 and 14 to somewhat less than that required for the hand, wrist and forearm enclosed within the init 10. This results in the hand, wrist and forearm being firmly, yet gently, secured between the two shells 12 and 14 when they are closed. As the total volume of the hand and the two liners 42 and 44 is slightly greater than the total volume of the two shells 12 and 14 when they are closed, the two shells 12 and 14 will have some clearance or gap 48 when closed with a hand and wrist placed therein. This assures that the hand placed therein does not fit loosely within the device, and that the fingers will remain properly positioned within the device after installation, thereby assuring that no damage will occur to the hand or fingers due to twisting and/or curling one or more fingers unnaturally while the present surgical device is installed upon the hand.

The slightly greater total volume of the hand and padding material 42 and 44 than the total internal volume of the two closed shells 12 and 14, also results in the two shells 12 and 14 being urged apart from one another when closed around a hand. The play allowed by the two loose hinge rings 36 and 38, in combination with the latch means used to close and latch the opposite closure edges 32 and 34, allows the gap or clearance 48 to expand to the limits defined by the hinge rings 36 and 38 and opposite latch members (discussed below), due to the resilience of the padding material 42 and 44 surrounding the hand, wrist and forearm.

A number of different types of closures may be incorporated with the present surgical device 10, as desired. The only critical factors are: (1) the closure means should be simple, economical, and reliable; (2) the closure means must be easy to sterilize, along with the remainder of the device; (3) the closure means must allow sufficient play between the two shells 12 and 14 for the resilience of the cushioning material to urge the two shells 12 and 14 apart from one another, in order to apply a constant gentle pressure to both sides of a hand "H" and wrist "W" enclosed within the unit 10; and (4) while at least one closure latch is required, preferably two such latches are used, corresponding with the preferred two hinge rings 36 and 38.

FIGS. 1 through 3 illustrate a first closure embodiment, wherein a first and a second over center latch, respectively 50 and! 52, extend from the closure edge 34 of the second shell 14. Wire clasp portions 54 and 56 of the two latches 50 and 52 engage The respective catches 58 and 60 extending from the latch or closure side or edge 32 of the first shell 12. The pivoting portions of the two latches 50 and 52 operate conventionally, snapping back over center away from their respective catches 58 and 60 on the first shell closure edge 32, to secure the two shell closure edges 32 and 34 together. The resilience of the cushioning liners 42 and 44 surrounding the hand within the closed shells 12 and 14, applies sufficient tensile force across the closed over center latches 50 and 52 to hold them in their latched configuration, without applying undue pressure to the hand within the surgical device.

Figure 4:
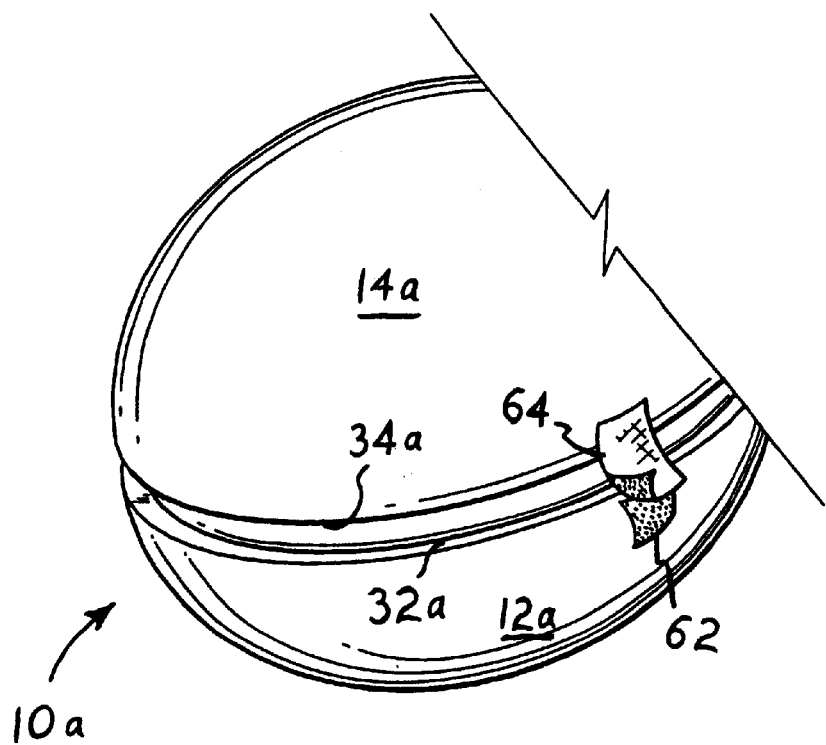
FIG. 4 is a partial perspective view of an alternate embodiment closure means for the surgical device, incorporating mating hook and loop fastening elements.
Figure 5:
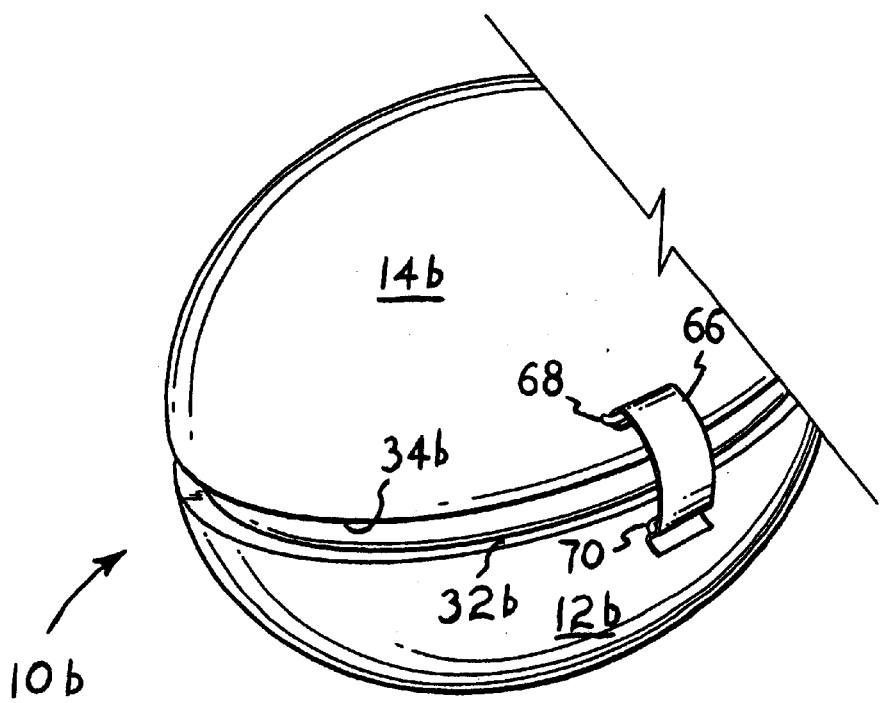
FIG. 5 is a partial perspective view of another alternate embodiment closure means for the surgical device, incorporating a resilient latch and catch.

FIGS. 4 through 6 show alternative closure means operable for advantageous use with the present hand, wrist and forearm protector. In FIG. 4, a portion of an alternative embodiment hand unit 10a is illustrated, with its two shells 12a and 14a in a closed position. It will be understood that the hand unit 10a of FIG. 4, as well as the hand unit 10b of FIG. 5 and 10c of FIG. 6, differ from the hand unit 10 of FIGS. 1 through 3 only in the configuration of the latch or closure mechanisms. Otherwise, each of the hand units 10, 10a, 10b, and 10c of the present disclosure, are substantially identical.

The closure means used for the unit 10a, comprises a first portion 62 of hook and loop fastener material permanently disposed upon the first shell 12a adjacent its closure edge 32a, and a second portion 64 of complementary hook and loop material: extending from the closure edge 34a of the second shell 14a. The second hook and loop material 64 overlaps the first hook and loop material 62 when the two shells 12a and 14a are closed, with the variable fit of the two hook and loop materials 62 and 64 providing the adjustable fit required for different hands and also adjusting: the pressure of the surgical unit 10a about the hand as desired.

Another latch alternative is illustrated for the unit, embodiment 10b of FIG. 5. In FIG. 5, a resilient leaf spring latch 66 is pivotally secured to a retainer 68 installed near the latch edge 34b of the second shell 14b. The leaf spring 66 may be formed of metal or suitable plastic material, as desired. The distal end of the leaf 66 hooks removably and resiliently under a catch 70 adjacent the latch edge 32b of the first shell 12b.

Finally, FIG. 6 illustrates yet another catch embodiment installed upon a surgical device 10c. In FIG. 6, a series of latch passages 72 are formed through the two shells 12c and 14c, adjacent their respective latch edges 32c and 34c. These latch passages 72 are similar to the hinge passages 40 of each of the surgical unit embodiments of the present invention. The latch assembly for the unit 10c comprises a split ring 74 which is removably installable through any two corresponding latch passages 72 of the two closure edges 32c and 34c of the device 10c.

The split ring 74 comprises two semicircular portions 76 and 78, joined together by a hinge pin 80. Mating distal faces 82 and, 84 of the respective portions 76 and 78 are flattened and provided with a series of mating serrations, as shown on the visible flattened face 84 of the split ring 74 of FIG. 6. The serrations of the two serrated faces 82 and 84 are oriented such that they grip one another when the ring 74 is closed, thus securing the two edges 32c and 34c of the unit 10c together when the ring 74 is opened, passed through any two corresponding latch passages 72, and closed to engage the complementary serrated faces 82 and 84. The pivot pin 80 is sufficiently tight as to preclude significant lateral play between the two ring portions 76 and 78, but the material of which the split ring 74 is formed (metal, or a sturdy plastic) provides sufficient resilience out of the plane of, the ring to allow the two serrated faces 82 and 84 to be disengaged from one another to open the ring 74, thereby allowing the ring 74 to be opened and removed from the passages 72 of the device 10c.

SUMMARY OF MAJOR ADVANTAGES OF THE INVENTION

Based on the above description those of ordinary skill in the art will recognize significant advantages attributable to the subject surgical invention. Without trying to list all of the advantages that are specifically disclosed or are inherently described in the disclosure, the addition of a positioning and isolation device for a patient during a surgical procedure to prevent inadvertent hand, wrist and/or forearm injuries is a significant improvement in the art.

The present invention precludes inadvertent injuries to the hand or hands, wrist(s) or forearm(s) of a patient undergoing surgery, by encasing and isolating the hand(s), wrist(s) and forearm(s) and precluding twisting or other deformation of the hand and resultant bone, tendon, and/or soft tissue damage. Several different embodiments of the present surgical device are provided, with the embodiments differing only in their latch configuration. The surgical device is easily applied to a patient, with; the patient's hand being gently but fly held in place by the cushioning material (gel packs, visco-elastic material, foams, etc.) lining the interiors of the two shells. The cushioning material also urge the two shells apart from one another, thus assuring that the relatively loose hinge and clasp structures of the device are held in tension to remain secured.

When the surgical procedure has been completed and the patient is regaining consciousness, or once the patient has been turned or moved to a position where the hand(s), wrist (s) and forearm(s) is/are no longer positioned beside the patient or otherwise where they are subject to pressure and deformation, the present surgical device may be facilely removed and sterilized for future use or discarded if it is designed for a single use. The present surgical device thus precludes injury to the hands, wrists and forearms of surgery patients, thereby eliminating subsequent postoperative problems and other negatives which have previously occurred as a result of damage to a patient's hand(s), waist(s) and forearm(s) as a result, of improper positioning during the surgery process.

Other advantages will be recognized by those of skill in the art but those above should demonstrate that the subject invention, as defined in the following claims, is a significant contribution to the art of medical surgery. Moreover, it is to be understood that the present invention is not limited to the embodiments described above, but encompasses any and all embodiments within the scope of the following claims.

We claim:

1. A surgical device for use with a patient during surgery, said surgical device comprising:

a first generally hemi-shell member operable to at least partially encompass a hand portion of a patient during a surgical procedure;

a second generally hemi-shell member also being operable to at least partially encompass the hand portion of the patient during the surgical procedure, said first member and said second member cooperating to operably form together a loose shell around the hand of the patient;

at least one hinge member loosely connecting each generally hemi-shell member together along mutually facing edges of said first and second hemi-shell members;

at least one closure member selectively connecting each of said hemi-shell members together along and edge generally opposed to said at least one hinge; and a cushion liner member disposed within each of said first and second hemi-shell members and wherein said first and said second hemi-shell members exhibit a clearance therebetween along each respective edge and being operable to receive and generally enrobe and isolate at least the patient's hand during a surgical procedure.

2. A surgical device for use with a patient during surgery as defined in claim 1 and further comprising:

each of said first and second hemi-shell members having a generally cylindrical extension operable to extend along and isolate a patient's wrist and at least a portion of a patient's forearm.

3. A surgical device for use with a patient during surgery as defined in claim 1 wherein said cushion liner comprises:

a visco-elastic member operable for conforming to the shape of a patient's hand while concomitantly providing support for the patient's hand.

4. A surgical device for use with a patient during surgery as defined in claim 1 wherein said cushion liners being disposed within each of said first and second hemi-shells further comprises:

a discardable sterile cloth member enrobing each of said cushion liners.

5. A surgical device for use with a patient during surgery as defined in claim 1 wherein said cushion liners being disposed within each of said first and second hemi-shells further comprises:

a discardable sterile paper member enrobing each of said cushion liners.

6. A surgical device for use with a patient during surgery as defined in claim 1 wherein:

each of said cushion liner members approximately fills said respective first and second generally hemi-shells such that a patients hand placed within and between said hemi-shells will be enrobed within said hemi-shells with a peripheral gap existing around the perimeter of opposing edge portions of said hemi-shells.

7. A surgical device for use with a patient during surgery as defined in claim 1 wherein each of said hemi-shells comprises:

a shell member that has a longitudinal dimension greater than a transverse dimension such that it generally conforms to the outer dimensions of a human hand and is dimensioned to extend around an outer perimeter of a human hand.

8. A surgical device for use with a patient during surgery as defined in claim 1 wherein said at least one hinge member comprises:

a pair of laterally spaced rings loosely fitted through opposing holes in the perimeter of one side of said first and said second hemi-shell members such that said hemi-shell members can be operably opened and closed in a manner similar to a clam shell to receive the hand of a patient.

9. A surgical device for use with a patient during surgery as defined in claim 8 wherein said at least one closure member comprises:

at least one resilient latch and catch fastening combination positioned generally opposite to said at least one hinge member.

10. A surgical device for use with a patient during surgery as defined in claim 8 wherein said at least one closure member comprises:

at least one split ring closure mechanism positioned generally opposite to said at least one hinge member.

11. A surgical device for use with a patient during surgery as defined in claim 1 wherein said at least one closure member comprises:

at least over the center latch mechanism positioned generally opposite to said at least one hinge member.

12. A surgical device for use with a patient during surgery as defined in claim 1 wherein said at least one closure member comprises:

at least one hook and loop fastening combination positioned generally opposite to said at least one hinge member.

13. A surgical device for use with a patient during surgery, said surgical device comprising:

a first generally rigid half-shell;

a second generally rigid half-shell dimensioned to be substantially similar and a mirror image of said first half-shell;

each said first and second half-shells having a concave wrist passage, a concave hand enclosure extending therefrom, a lateral hinge edge, and a closure edge opposite said hinge edge;

at least one hinge loosely connecting each said first and second half-shell together along said hinge edge;

at least one closure releaseably connecting each said first and second half-shells together along said closure edge; and a cushioned liner disposed in each said first and second half-shells for stabilizing a patient's hand placed therein and for urging said first and said second half-shells apart from one another in order to stabilize each of said half-shells when closed.

14. A surgical device for use with a patient during surgery as defined in claim 13 wherein said cushioned liner within each of said first and second half-shells comprises:

a visco-elastic member operable to assume the impression of a patient's hand when enclosed within said first and second half-shells.

15. A surgical device for use with a patient during surgery as defined in claim 14 and wherein:

each of said visco-elastic members are enrobed within a discardable sterile member.

* * * * *